(12) United States Patent
Beck et al.

(10) Patent No.: US 9,528,965 B2
(45) Date of Patent: Dec. 27, 2016

(54) SYSTEM AND A METHOD OF INSPECTING A ROTARY PART TO BE MONITORED THAT IS ARRANGED IN A MECHANICAL MEMBER

(71) Applicant: AIRBUS HELICOPTERS, Marignane (FR)

(72) Inventors: Philippe Beck, Jouques (FR); Andre Jean Baixas, Vitrolles (FR); Sebastien Bernier, Pertuis (FR); Eric Biletta, Pourrieres (FR); Olivier Molinas, La Fare les Oliviers (FR)

(73) Assignee: Airbus Helicopters, Marignane (FR)

( * ) Notice: Subject to any disclaimer, the term of this patent is extended or adjusted under 35 U.S.C. 154(b) by 355 days.

(21) Appl. No.: 14/323,454

(22) Filed: Jul. 3, 2014

(65) Prior Publication Data
US 2015/0007660 A1 Jan. 8, 2015

(30) Foreign Application Priority Data

Jul. 3, 2013 (FR) ..................................... 13 01575

(51) Int. Cl.
*G01N 29/24* (2006.01)
*G01N 29/04* (2006.01)
(Continued)

(52) U.S. Cl.
CPC ............ *G01N 29/24* (2013.01); *G01M 13/028* (2013.01); *G01N 29/04* (2013.01); *G01N 29/225* (2013.01);
(Continued)

(58) Field of Classification Search
CPC .... G01M 13/028; G01N 29/225; G01N 29/04; G01N 29/24; G01N 2291/044; G01N 2291/2693; G01N 2291/0289; G01N 2291/2636
(Continued)

(56) References Cited

U.S. PATENT DOCUMENTS 3,841,764 A 10/1974 Snell et al.
4,245,624 A * 1/1981 Komiya ............. A61B 1/00098
600/106
(Continued)

FOREIGN PATENT DOCUMENTS

DE 29812120 * 11/1999
EP 2042076 A2 4/2009
(Continued)

OTHER PUBLICATIONS

French Search Report for FR 1301575, Completed by the French Patent Office on Mar. 18, 2014, 7 Pages.
(Continued)

*Primary Examiner* — J M Saint Surin
(74) *Attorney, Agent, or Firm* — Brooks Kushman P.C.

(57) ABSTRACT

A system and method for inspecting a part to be monitored that is arranged inside a mechanical member, said part to be monitored including a plane wall and a curved wall presenting an angle between them. The system comprises a probe endoscope (20) carrying a head (30), said head (30) presenting a plane face (31) that is suitable for being pressed against said plane wall, said head (30) having an ultrasound probe (35) and at least one magnet (36) flush with said plane face (31), said head (30) having a curved face (32) that is perpendicular to the plane face (31) and that matches the shape of the curved wall of the part to be monitored, the plane face (31) and the curved face (32) forming an
(Continued)

L-shaped structure that is suitable for being held against the part to be monitored via each magnet (36), while allowing said part to be monitored to rotate relative to said head (30).

16 Claims, 4 Drawing Sheets

(51) Int. Cl.
*G01M 13/02* (2006.01)
*G01N 29/22* (2006.01)

(52) U.S. Cl.
CPC . *G01N 2291/0289* (2013.01); *G01N 2291/044* (2013.01); *G01N 2291/2636* (2013.01); *G01N 2291/2693* (2013.01)

(58) Field of Classification Search
USPC .......................................................... 73/632
See application file for complete search history.

(56) References Cited

U.S. PATENT DOCUMENTS

| | | | | |
|---|---|---|---|---|
| 5,396,880 | A * | 3/1995 | Kagan | A61B 1/0051 600/109 |
| 8,499,622 | B2 | 8/2013 | Gaisnon et al. | |
| 8,558,878 | B2 | 10/2013 | Bousquet et al. | |
| 2006/0069313 | A1* | 3/2006 | Couvillon | A61B 5/064 600/179 |
| 2006/0074383 | A1* | 4/2006 | Boulais | A61B 1/0052 604/95.04 |
| 2006/0142660 | A1* | 6/2006 | Maschke | A61N 1/056 600/466 |
| 2006/0162456 | A1 | 7/2006 | Kennedy et al. | |
| 2008/0312848 | A1 | 12/2008 | Fogarty et al. | |
| 2012/0167688 | A1 | 7/2012 | Minachi et al. | |

FOREIGN PATENT DOCUMENTS

| | | |
|---|---|---|
| EP | 2042076 A3 | 5/2010 |
| EP | 2192406 | 6/2010 |
| JP | H07174739 | 7/1995 |
| JP | 2003010104 * | 1/2003 |
| KR | 20100078441 | 7/2010 |
| WO | 2011004101 | 1/2011 |

OTHER PUBLICATIONS

NPL/Website—http://www.olympusims.com/fr/erw/ Olympus, You Vision, Our Future, Industrial NDT Systems, Copyright 2010 by Olympus NDT, 3 Pages, "In-Line ERW Tube Inspection."

European Search Report Dated Oct. 7, 2014, Application No. EP 14 00 2080, 6 Pages.

* cited by examiner

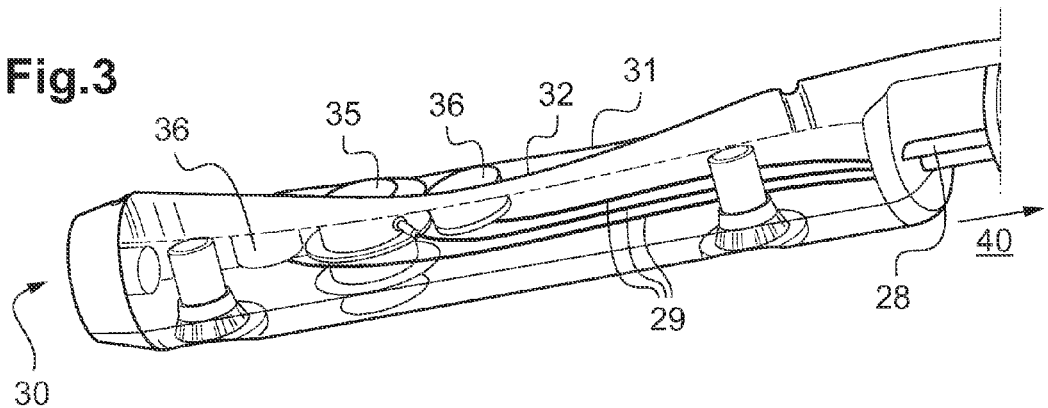
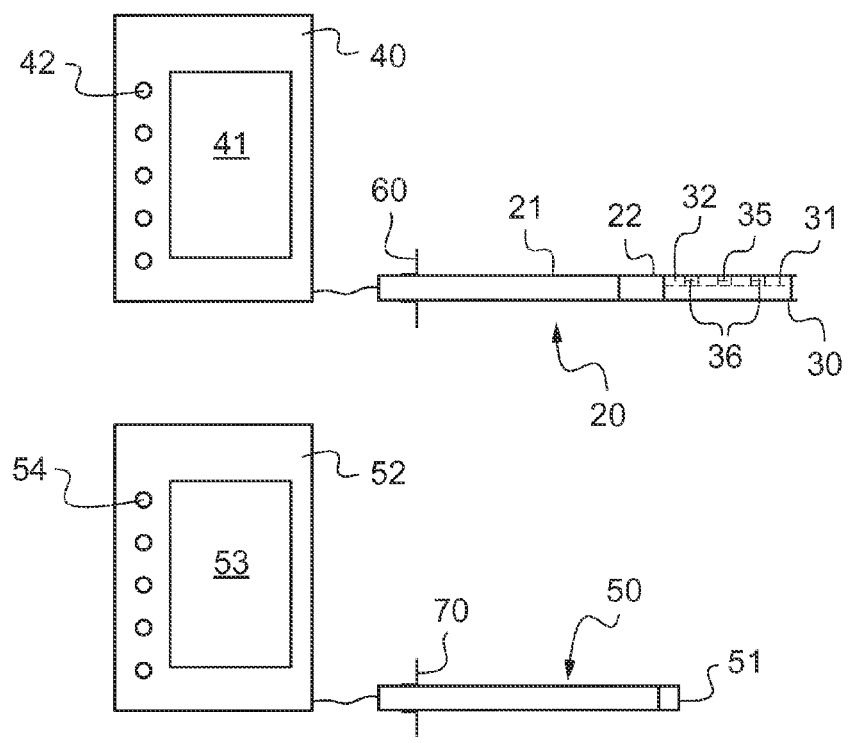

SYSTEM AND A METHOD OF INSPECTING A ROTARY PART TO BE MONITORED THAT IS ARRANGED IN A MECHANICAL MEMBER

CROSS REFERENCE TO RELATED APPLICATION

This application claims priority to French patent application No. FR 13 01575 filed on Jul. 3, 2013, the disclosure of which is incorporated in its entirety by reference herein.

BACKGROUND OF THE INVENTION (1) Field of the Invention

The present invention relates to a system and to a method of inspecting a rotary part to be monitored, the part to be monitored being arranged inside a mechanical member. More particularly, the mechanical member may be a power transmission train, possibly a main gearbox of a vehicle such as an aircraft.

(2) Description of Related Art

Such a main gearbox may be interposed between a power plant and at least one rotor or a rotary shaft of a vehicle. A main gearbox may incorporate at least one speed reduction stage that has at least one rotary part to be monitored. By way of example, such a part to be monitored is provided with a shaft carrying a gear.

The shaft may include segments that are welded to one another. The shaft is likely to wear during its use. A user thus verifies the physical integrity of the rotary part to be monitored, and in particular of the welds of the part to be monitored. In particular, the inspection operation consists in verifying the absence of cracks on the part to be monitored.

However, the part to be monitored is arranged inside the main gearbox, in a zone that is practically inaccessible. It should be understood that it is thus difficult to inspect the part to be monitored in non-destructive manner.

In a first method, an operator removes the main gearbox from the vehicle, then dismantles the MGB. The operator then inspects the part to be monitored using an auxiliary method, e.g. a magnetoscopic test method.

That first method requires the transmission gearbox to be dismantled, which can lead to the main gearbox being out of service for a relatively long period. For a period of about two weeks, for example.

In a second method, an operator drains the main gearbox, and then removes the sump of the main gearbox so as to access the part to be monitored.

The operator then inspects the part to be monitored by inspecting it with a method that uses eddy currents.

That second method may require the main gearbox to be out of service for a moderate duration, e.g. about 8 hours.

The first and second methods are advantageous but they take the mechanical member to be inspected, and consequently also the vehicle having the mechanical member, out of service for a non-negligible duration. Furthermore, those methods present a risk of damaging the parts to be dismantled and/or inspected. The second method also runs the risk of forgetting a part inside the main gearbox.

The Japanese document published under reference 07-174739, on Jul. 14, 1995, describes a device that is provided with a carriage carrying a plurality of probes. Springs press the probes against the surface of the part to be monitored.

Document KR 2010 0078441 describes a method of inspecting an axle by ultrasound. The method implements a system including, in particular, a detection device, a device for removing oil, and a device for feeding oil.

Document EP 2 192 406 describes copying apparatus provided with a carriage carrying a flaw detector for detecting flaws by ultrasound.

Ultrasound probes may thus be used for attempting to detect flaws. Such a probe emits a signal towards the part to be monitored. As a function of the echo received in return by the probe, an operator can determine whether a part presents a flaw. The echo may also convey other information, e.g. relating to a change in the shape of a part.

Any flaw and information deduced from the echo is referred to below as a "flaw" for convenience.

However, it can be difficult to use such a probe. Specifically, the probe should cause waves to propagate in constant manner relative to the part to be monitored, in order to provide information that is usable.

In addition, by way of information and in a field that is unrelated to the invention, a device is known for treating prostate cancer by ultrasound. A probe emits ultrasound waves for treating a prostate. The probe may be arranged on the end of an endoscope. The end may present a shape that is concave around the probe, so as to avoid dispersing the emitted waves.

The device does not provide any teaching for detecting a flaw on an internal rotary part of a mechanical member.

Internet address http://www.olympus-ims.com/fr/erw/ describes an inspection system for inspecting tubes that are electrical resistance welded. That system uses multi-element ultrasound technology for inspecting a weld by means of a rotating head. The ability of the head to rotate allows each probe to move independently from −120° to 120° along the weld to be inspected.

Documents US 2006/162456, US 2012/167688, US 2008/312848, WO 2011/004101, and EP 2 042 076 are remote from the invention.

Document US 2006/162456 describes a system for inspecting a stationary stringer. That system presents an instrument that is trapezoidal.

Document US 2012/167688 presents a device that is fastened in permanent manner to a tube so as to inspect its thickness.

Document US 2008/312848 describes a system that is provided with lugs and with a probe.

Document WO 2011/004101 presents a device for inserting into an endoscope orifice. The device includes a stick carrying a pivotable finger. The pivotable finger extends from an end provided with a probe-support blade to an end carrying a movable bearing skid.

Document EP 2 042 076 presents a steerable endoscope.

BRIEF SUMMARY OF THE INVENTION

An object of the present invention is thus to propose a system for inspecting a rotary part to be monitored that is arranged inside a mechanical member.

Thus, the invention relates to a system for inspecting a rotary part to be monitored that is arranged inside a mechanical member, the part to be monitored including a plane wall and a curved wall, presenting an angle between them. By way of example, the part to be monitored is a part of a main gearbox having a rotational symmetry.

The system comprises a probe endoscope carrying a head, the head presenting a plane face that is suitable for being pressed against said plane wall, the head having an ultrasound probe and at least one magnet flush with the plane face, the head having a curved face that is perpendicular to the plane face and that matches the shape of the curved wall of the part to be monitored, the plane face and the curved face forming an L-shaped structure that is suitable for being held against the part to be monitored via each magnet, while allowing the part to be monitored to rotate relative to the head of the probe endoscope.

Furthermore, the probe endoscope includes a "rigid endoscope tube" that is followed by a "hinged endoscope tube" carrying the head. Thus, the hinged endoscope tube may possess a tip that is deflected.

The rigid endoscope tube makes it possible to direct the probe endoscope along a preferred direction. In contrast, the hinged endoscope tube makes it possible to adjust the position of the head, so as to position it against the part to be monitored.

Consequently, the system equips an endoscope with an ultrasound probe so as to obtain a probe endoscope. The probe endoscope may be inserted directly into the mechanical member with very little dismantling of the mechanical member and without the need for it to be drained in order to proceed with inspecting the part to be monitored. The system thus takes the mechanical member out of service for a shorter time.

Inserting an endoscope into a mechanical member that is not designed for this purpose, such as a main gearbox, is not at all obvious. However, as described below, the endoscope may be inserted via existing orifices in the mechanical member.

Furthermore, using a probe endoscope to perform an inspection by ultrasound is not obvious in that the ultrasound probe must be positioned correctly relative to the rotary part to be monitored. The probe endoscope of the invention makes it possible to remedy this problem by synergy between the plane face of the head, the curved face of the head, and the use of at least one magnet.

Each magnet makes it possible to press the head against the part to be monitored. The plane face and the curved face are themselves shaped to match the shape of the part to be monitored, and, by way of example, they are shaped to match the shape of a shoulder of the part to be monitored that has been welded. Consequently, the head positions the ultrasound probe appropriately relative to the part to be monitored. Furthermore, the part to be monitored may be rotated so as to inspect it, the magnets not preventing such rotation of the part to be monitored relative to the ultrasound probe.

The system may also include one or more of the following characteristics.

Thus, the probe endoscope may include steering means for steering the hinged endoscope tube.

By way of example, the steering means comprises at least one flexible connection that is connected to the hinged endoscope tube. An operator directs the head of the probe endoscope by steering the flexible connection.

Conventional steering means for steering endoscopes may be used.

In addition, the head may include two magnets that are arranged one on either side of said ultrasound probe.

Thus, the positioning of the ultrasound probe is optimized since the head is connected to the part to be monitored by two magnets on either side of the ultrasound probe. The stability of the ultrasound probe relative to the part to be monitored thus tends to be optimized.

Furthermore, the system may include guide means for guiding the probe endoscope. By way of example, the guide means for guiding towards the zone to be inspected comprises a tube that is fastened to the mechanical member and that is passed through by the probe endoscope. The probe endoscope can thus be inserted more easily into the mechanical member. The probe endoscope may be held in position in the guide means.

In addition, the probe endoscope may include a delivery tube for delivering an ultrasonic couplant, which delivery tube opens out in the head so as to guarantee good transmission of the ultrasound into the part to be monitored. In another aspect, the system includes an ultrasound station that is separate and that is connected to the ultrasound probe.

The ultrasound station communicates with the ultrasound probe, analyses the signal received, and displays the results of the analysis.

An operator thus positions the probe endoscope, then proceeds to inspect the part to be monitored by using the ultrasound station. Reference may be made to the literature to obtain a description of such an ultrasound station.

In addition, the system may include a viewing endoscope that is provided with a video camera so as to view the position of the head of the probe endoscope.

Specifically, the probe endoscope passes through the mechanical member so as to reach the part to be monitored. Its insertion may be guided by guide means so as to make it easier to put it into place. When the probe endoscope is inserted into the mechanical member, an operator may incline the head carrying the ultrasound probe, so as to position it against the part to be monitored.

Under such circumstances, a viewing endoscope is possibly used in parallel with the probe endoscope, so as to assist an operator in positioning the ultrasound probe in the required manner.

The system may also include a display unit that is connected to the viewing endoscope so as to display, on a screen, the images picked up by the viewing endoscope.

Finally, the probe endoscope possibly includes fastener means for fastening to a casing of the mechanical member during an inspection operation.

In addition, a viewing endoscope may include fastener means for fastening to a casing.

The invention also provides a mechanical member that is provided with a rotary part to be monitored that is inaccessible from the outside of the mechanical member, the mechanical member including at least one removable lubrication nozzle that is fastened to a casing of the mechanical member.

Under such circumstances, the mechanical member includes a system of the above-mentioned type that is arranged on the mechanical member only while inspecting the part to be monitored. Thus, the probe endoscope is inserted into the mechanical member instead of the lubrication nozzle, during inspection only.

The invention also relates to a vehicle provided with the mechanical member.

The invention also provides a method of inspecting a part to be monitored of such a mechanical member. In the method:

the lubrication nozzle is removed, and guide means might be installed;

the probe endoscope is inserted instead of the lubrication nozzle, where appropriate through the guide means;

the probe endoscope is steered so as to press the plane face of the head against a plane wall of the part to be monitored, and so as to place the curved face of the head against a curved wall of the part to be monitored;

the ultrasound probe is activated so as to acquire measurement data that makes it possible to determine the presence of a possible flaw; and the part to be monitored is caused to rotate.

Consequently, the method makes it easy to inspect a mechanical member. The method does not require draining or removing a main gearbox, since it requires only a lubrication nozzle to be replaced by a probe endoscope.

For a system that is provided with a probe endoscope and with a viewing endoscope:

two lubrication nozzles are removed, and at least one guide means might be installed;

the probe endoscope is inserted instead of one lubrication nozzle, and a viewing endoscope is inserted instead of the other lubrication nozzle, where appropriate through guide means;

under the surveillance of the viewing endoscope, the probe endoscope is steered so as to press the plane face of the head against a plane wall of the part to be monitored, and so as to place the curved face of the head against a curved wall of the part to be monitored; and the ultrasound probe is activated so as to acquire measurement data that makes it possible to determine the presence of a possible flaw; and the part to be monitored is caused to rotate.

The probe endoscope and/or the viewing endoscope may be fastened to a casing of the mechanical member during the acquisition of the measurements.

BRIEF DESCRIPTION OF THE SEVERAL VIEWS OF THE DRAWINGS

The invention and its advantages appear in greater detail in the context of the description below with reference to the accompanying figures, in which:

FIG. 3 is a view of the head of a probe endoscope;

FIG. 4 is a diagrammatic representation of a system provided with a probe endoscope and with a viewing endoscope.

DETAILED DESCRIPTION OF THE INVENTION

Elements that are present in more than one of the figures are given the same references in each of them.

Figure 1:
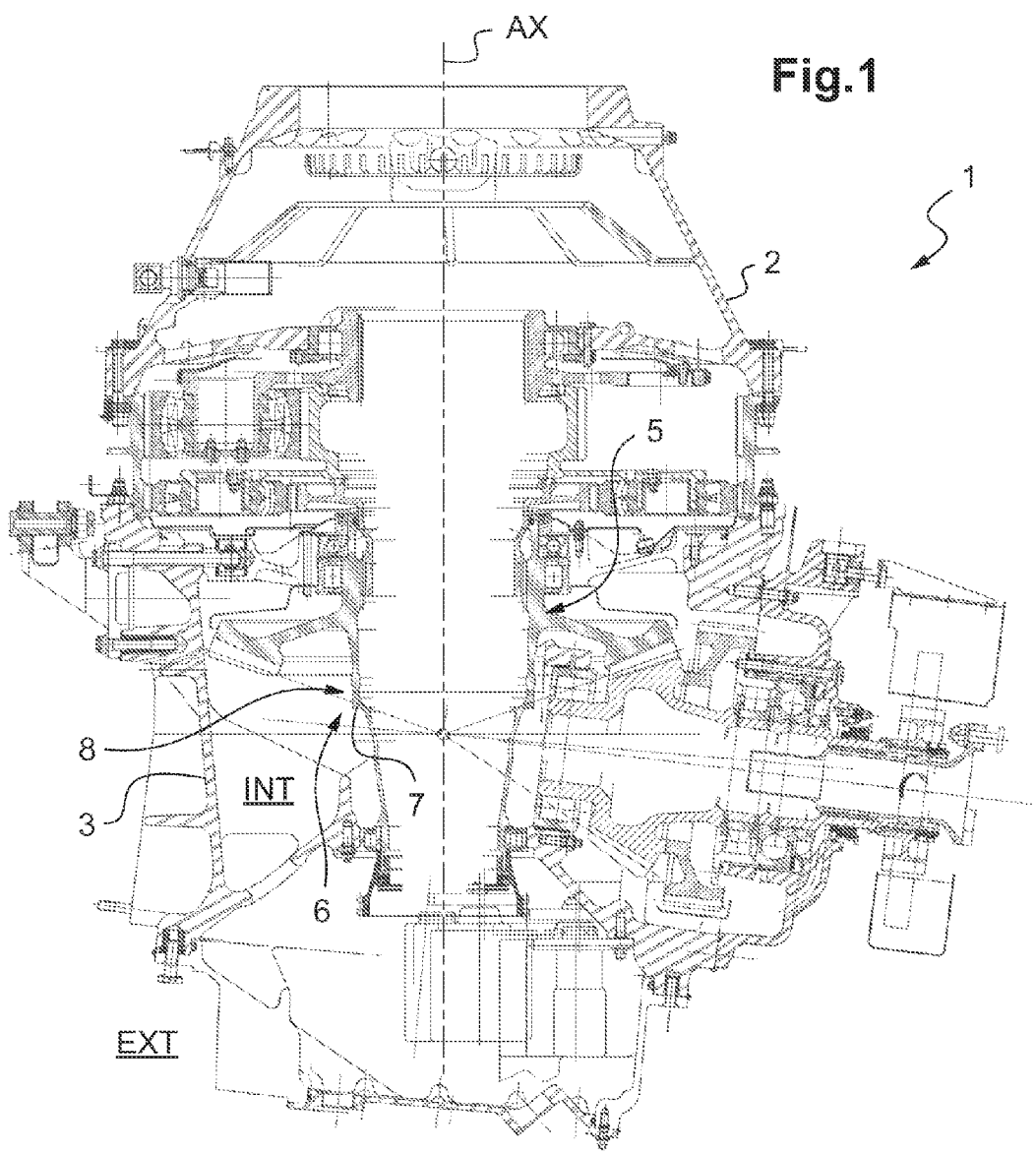
FIG. 1 is a section of a mechanical member to be inspected.

FIG. 1 presents a vehicle 1 that is provided with a mechanical member 2. The other members of the vehicle are not shown diagrammatically so as to avoid pointlessly overcrowding FIG. 1.

The mechanical member may be a main gearbox that is interposed between at least one rotor and at least one engine of an aircraft, for example.

The mechanical member 2 includes a part to be monitored 5 that is arranged in the inside INT of a casing 3. As a result, the part to be monitored 5 is not accessible from the outside EXT of the mechanical member 2. In operation, the part to be monitored rotates about an axis that is referred to as the "working axis AX" for convenience.

The part to be monitored 5 includes, in particular, a zone 6 that has been subject to welding, for example. The zone 6 includes a cylindrical shoulder comprising a plane wall 7 and a curved wall 8 describing a cylinder. The mechanical member may be provided with at least one lubrication nozzle, not shown in FIG. 1, for spraying a lubricant inside the mechanical member. The casing 3 may thus present one orifice per lubrication nozzle.

The mechanical member is thus provided with a system 10 for inspecting the part to be monitored 5. This system is removable so as to be in place only while the part to be monitored 5 is being inspected.

Figure 2:
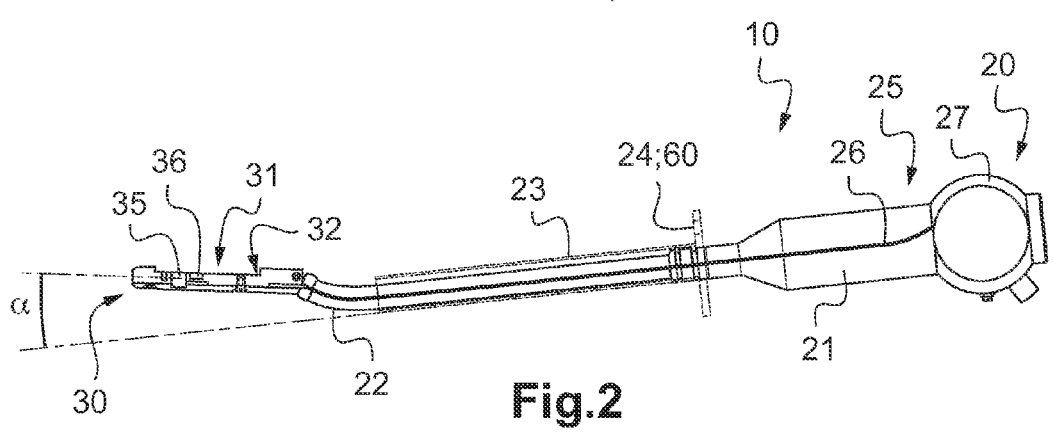
FIG. 2 is a section of a probe endoscope.

With reference to FIG. 2, the system 10 is provided with a probe endoscope 20.

The probe endoscope has a head 30 carrying an ultrasound probe 35.

With reference to FIG. 3, the head 30 is provided with a plane face 31. The ultrasound probe 35 thus opens out in the plane face 31, so as to emit ultrasound towards a part to be monitored, and so as to receive the resulting echoes.

Furthermore, the head is also provided with at least one magnet 36 that opens out in the plane face 31, so as to press the plane face 31 of the head 30 against the plane wall 7 of the part to be monitored 5. Two magnets 36 may be arranged on either side of the ultrasound probe 35, so as to optimize the positioning of the ultrasound probe 35 relative to the part to be monitored 5.

Furthermore, the head 30 presents a curved face 32 that matches the curved wall 8 of the part to be monitored. The curved face 32 extends in elevation from the plane face 31, presenting an angle relative to the plane face 31. In particular, the curved face may be perpendicular to the plane face. The curved face thus presents a concave shape that matches the convex shape of the curved wall 8.

As a result, the plane face and the curved face form a structure that is substantially L-shaped for positioning against a corner of the part to be monitored. The term "having an L-shape" means that each section in elevation of said structure is substantially L-shaped.

The head may thus be pressed against the part to be monitored 5 via each magnets 36, while leaving the part to be monitored 5 free to rotate about the working axis AX.

The ultrasound probe 35 and the magnets 36 may be connected via wired or wireless connections 29 to a control unit 40 that is not shown in FIG. 3. The control unit is referred to below as "an ultrasound station".

In addition, the probe endoscope 20 has a delivery tube 28 for delivering ultrasonic couplant, which tube opens out in the head 30. The tube 28 makes it possible to deliver an ultrasonic couplant to the head 30. The ultrasonic couplant may be oil.

In order to carry the head 30, the probe endoscope 20 is provided with a rigid endoscope tube 21 that is extended by a hinged endoscope tube 22 carrying the head 30. Thus, the hinged endoscope tube 22 makes it possible to move the head 30 through an angular sector a. The hinged endoscope tube may be connected to the head 30 via a hinge that leaves the head a degree of freedom in turning, e.g. making it possible to move the head 30 towards the part to be monitored 5 under the effect of the magnets 36.

To this end, the probe endoscope includes steering means 25 for steering the hinged endoscope tube 22. The steering means 25 shown in FIG. 2 comprise a flexible connection 26 that is connected to an actuator 27. By steering the actuator 27, an operator can move the hinged endoscope tube and thus the head 30.

Furthermore, the system 10 may include guide means 24 for guiding the probe endoscope 20. By way of example, the guide means may extend over the length of the rigid endoscope tube. Furthermore, the guide means may include fastener means for fastening the probe endoscope to the casing of the mechanical member.

In addition, FIG. 4 shows a system 10 that is provided with an ultrasound station 40 that is connected to the probe endoscope 20. The ultrasound station 40 may be at a distance from the mechanical member, being connected via wired or wireless connections to the probe endoscope 20.

The ultrasound station comprises a screen 41 and possibly a plurality of buttons 42. The function of the ultrasound station is to cause ultrasound to be emitted via the ultrasound probe 35 of the probe endoscope, and to display a representation of the measurement signal picked up by the ultrasound probe 35.

In addition, the system 10 is advantageously provided with a viewing endoscope 50 carrying a video camera 51, and with a display unit 52 connected to the viewing endoscope 50. The display unit may comprise a screen 53 presenting the images taken by means of the video camera 51, and a plurality of buttons 54.

Furthermore, the probe endoscope 20 and/or the viewing endoscope 50 may include fastener means 60, 70 for fastening to a casing 3.

FIGS. 5 to 8 show the inspection method of the invention.

Figure 5:
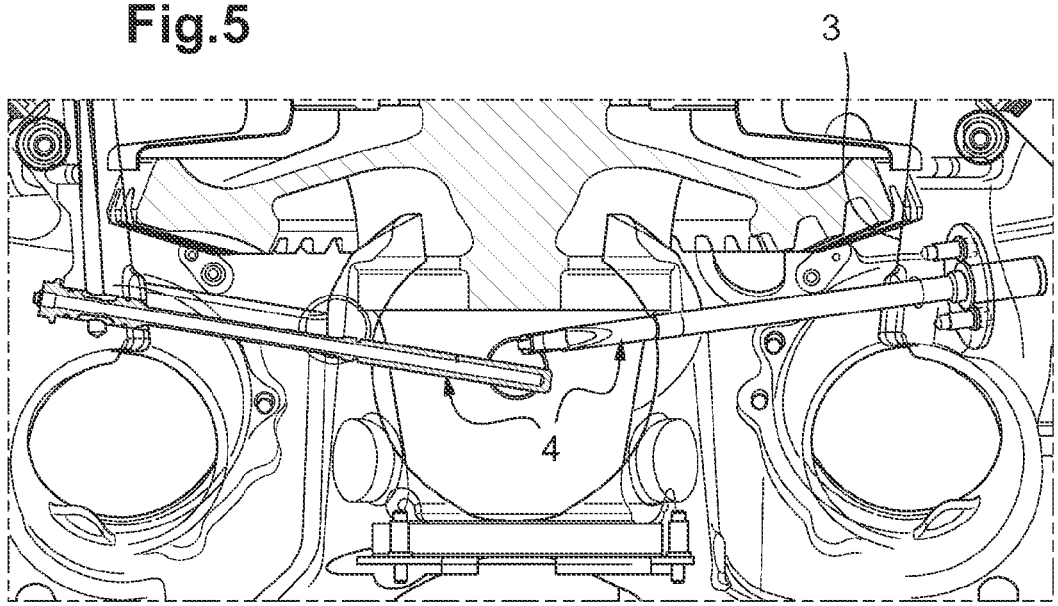
FIGS. 5 to 8 are views showing the method that is implemented.

With reference to FIG. 5, an operator inhibits the lubrication system by removing at least the lubrication nozzle 4 of the mechanical member. This operation makes at least one orifice available in the casing 3 of the mechanical member. The operator may then install respective guide means for guiding each endoscope.

Figure 6:
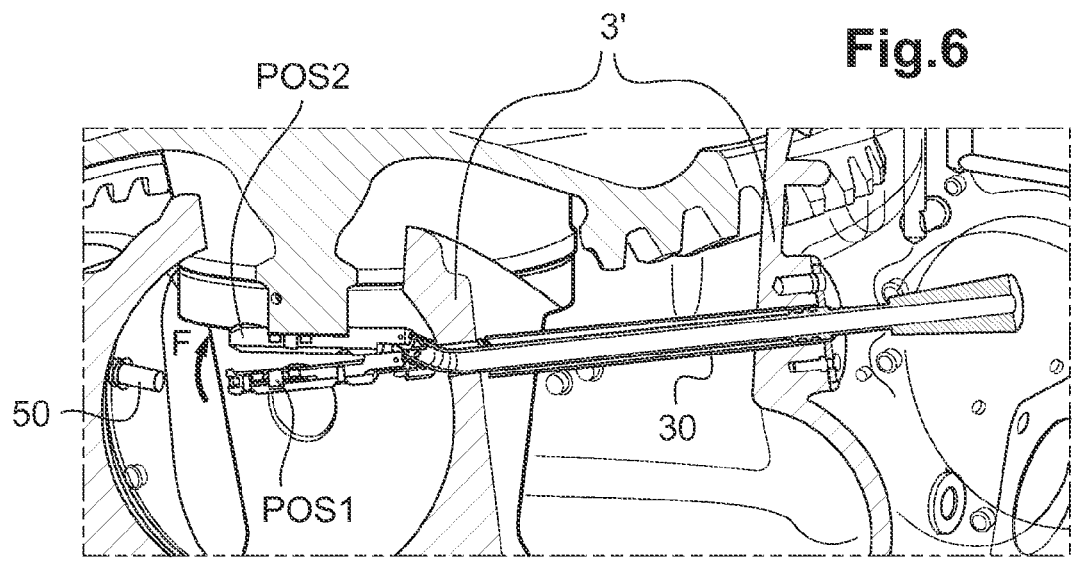

Under such circumstances, and with reference to FIG. 6, the operator inserts the probe endoscope 20 into the mechanical member 2, the probe endoscope passing through the walls 3' of the mechanical member 2.

The operator begins by inserting the viewing endoscope 50 into the casing 3 so as to visually monitor the manipulation of the probe endoscope 20.

Figure 7:
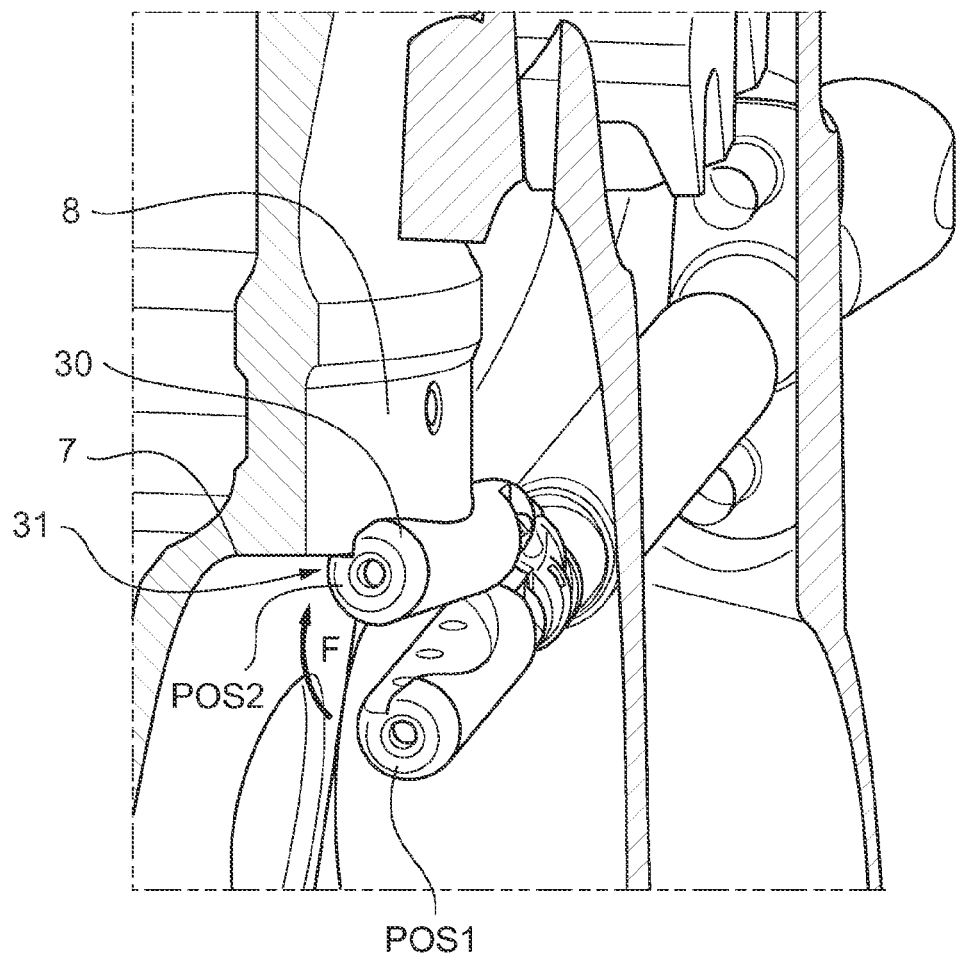
Figure 8:
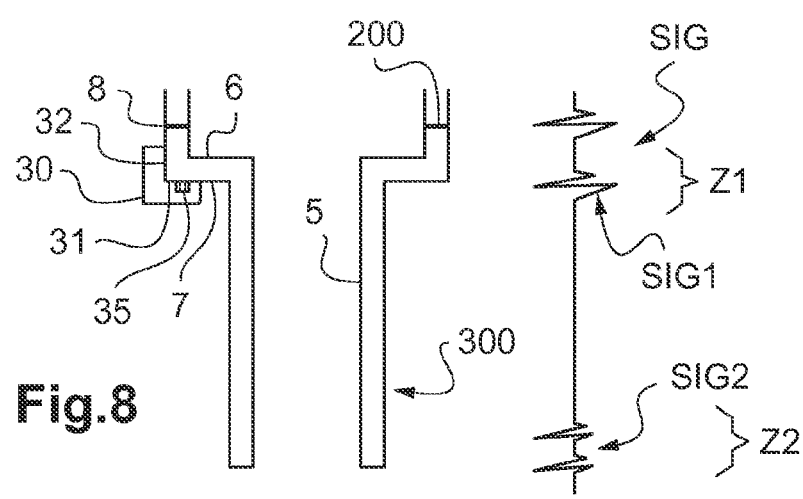

With reference to FIGS. 6 and 7, the operator steers the probe endoscope 20 so as to move it along arrow F from a first position POS1, obtained as a result of inserting the probe endoscope into the mechanical member, towards a second position POS2.

In the second position POS2, the plane face 31 of the head 30 is against a plane wall 7 of the part to be monitored 5, and the curved face 32 of the head 30 is against a curved wall 8 of the part to be monitored 5.

The positioning of the head 30 may be monitored by means of the viewing endoscope.

At this stage, the inspection operation may begin. Thus, the operator may cause the part to be monitored to rotate by causing a rotor that is connected to the mechanical member to rotate, for example.

The ultrasound probe 35 then makes it possible to display a measurement signal SIG on the ultrasound station. As a function of the displayed signal, the operator may deduce therefrom the presence of a flaw. For example, the presence of an echo SIG1 in an inspection window Z1 may be indicative of a flaw in a weld bead 200. Conversely, the presence of an echo SIG2 in an inspection window Z2 may be indicative of an absence of a flaw in the bottom 300 of the part to be monitored.

The ultrasound probe may emit ultrasound before the part to be monitored is caused to rotate, and vice versa.

During the inspection operation, an ultrasonic couplant may be injected so as to facilitate the passage of the ultrasound emitted and received by the probe endoscope.

Naturally, the present invention may be subjected to numerous variations as to its implementation. Although several embodiments are described above, it should readily be understood that it is not conceivable to identify exhaustively all possible embodiments. It is naturally possible to envisage replacing any of the means described by equivalent means without going beyond the ambit of the present invention.

What is claimed is:

1. A system for inspecting a rotary part to be monitored that is arranged inside a mechanical member, said part to be monitored including a plane wall and a curved wall, presenting an angle between them, the system comprising a probe endoscope that is provided with a rigid endoscope tube followed by a hinged endoscope tube carrying a head, said head presenting a plane face that is suitable for being pressed against said plane wall, said head having an ultrasound probe and at least one magnet flush with said plane face, said head having a curved face that is perpendicular to the plane face and that matches the shape of the curved wall of the part to be monitored, the plane face and the curved face forming an L-shaped structure that is suitable for being held against the part to be monitored via each magnet, while allowing said part to be monitored to rotate relative to said head.

2. A system according to claim 1, wherein said probe endoscope includes steering means for steering the hinged endoscope tube.

3. A system according to claim 2, wherein said steering means comprises a flexible connection that is connected to the hinged endoscope tube.

4. A system according to claim 1, wherein said head includes two magnets that are arranged one on either side of said ultrasound probe.

5. A system according to claim 1, wherein said system includes guide means for guiding the probe endoscope.

6. A system according to claim 1, wherein said probe endoscope includes a delivery tube for delivering an ultrasonic couplant, which delivery tube opens out in said head so as to guarantee good transmission of the ultrasound into the part to be monitored.

7. A system according to claim 1, wherein said system includes an ultrasound station that is separate and that is connected to said ultrasound probe, said ultrasound station controlling said ultrasound probe.

8. A system according to claim 1, wherein said system includes a viewing endoscope that is provided with a video camera so as to view the position of the head of the probe endoscope.

9. A system according to claim 1, wherein said system includes a display unit that is connected to said probe endoscope.

10. A system according to claim 1, wherein said probe endoscope includes fastener means for fastening to a casing.

11. A system according to claim 10, wherein said probe endoscope includes fastener means for fastening to a casing.

12. A mechanical member that is provided with a rotary part to be monitored that is inaccessible from the outside of the mechanical member, said mechanical member including at least one removable lubrication nozzle that is fastened to a casing of the mechanical member, the mechanical member including a system according to claim 1, said probe endoscope being inserted into said mechanical member instead of said lubrication nozzle, during inspection only.

13. A vehicle including a mechanical member according to claim 12.

14. A method of inspecting a rotary part to be monitored of a mechanical member according to claim 12, wherein:
said lubrication nozzle is removed;
the probe endoscope is inserted instead of the lubrication nozzle;

the probe endoscope is steered so as to press the plane face of the head against a plane wall of the part to be monitored, and so as to place the curved face of the head against a curved wall of the part to be monitored;

the ultrasound probe is activated so as to acquire measurement data that makes it possible to detect a possible flaw; and the part to be monitored is caused to rotate.

15. A method according to claim 14, wherein:

two lubrication nozzles are removed;

the probe endoscope is inserted instead of one lubrication nozzle, and a viewing endoscope is inserted instead of a second lubrication nozzle;

under the surveillance of the viewing endoscope, the probe endoscope is steered so as to press the plane face of the head against a plane wall of the part to be monitored, and so as to place the curved face of the head against a curved wall of the part to be monitored; and the ultrasound probe is activated so as to acquire measurement data that makes it possible to detect a possible flaw; and the part to be monitored is caused to rotate.

16. A method according to claim 14, wherein each endoscope is fastened to a casing of the mechanical member.

* * * * *